United States Patent [19]

Plueddemann

[11] 4,370,255
[45] Jan. 25, 1983

[54] STABILIZATION OF AQUEOUS SILICATES USING ALKALI SILICONATES OF SILYLALKYL PHOSPHONATES

[75] Inventor: Edwin P. Plueddemann, Midland, Mich.

[73] Assignee: Dow Corning Corporation, Midland, Mich.

[21] Appl. No.: 245,059

[22] Filed: Mar. 18, 1981

Related U.S. Application Data

[63] Continuation of Ser. No. 891,584, Mar. 30, 1978, abandoned.

[51] Int. Cl.³ ............................................... C09K 3/00
[52] U.S. Cl. .............................. 252/389 A; 252/396; 252/400 A; 252/78.3; 252/78.5; 422/15; 556/405; 252/389 R
[58] Field of Search ............... 260/448.2 R, 448.2 B, 260/448.2 N, 448.2 S, 448.8 R; 252/389 A, 180, 181, 400 A, 407, 78.3, 78.5, 75, 68, 389 R, 396, 82, 86, 87; 422/15; 106/14.12; 891/584; 556/404, 405

[56] References Cited

U.S. PATENT DOCUMENTS

| | | | |
|---|---|---|---|
| 3,198,820 | 8/1965 | Pines et al. | 260/448.2 |
| 3,312,622 | 4/1967 | Pines | 252/389 R |
| 3,337,496 | 8/1967 | Pines et al. | 260/46.5 |
| 3,341,469 | 9/1967 | Pines et al. | 252/389 R |
| 3,948,964 | 4/1976 | Barfurth et al. | 260/448.8 R |
| 3,960,576 | 6/1976 | Carter et al. | 252/389 A |
| 4,084,951 | 4/1978 | Gregory | 556/405 |
| 4,093,641 | 6/1978 | Plueddemann | 556/405 |
| 4,177,200 | 12/1979 | Razzano et al. | 556/405 |

*Primary Examiner*—J. L. Barr
*Attorney, Agent, or Firm*—Robert L. McKellar

[57] ABSTRACT

What is disclosed are novel compositions of matter which are alkali siliconate silylalkylphosphonates which are capable of stabilizing water soluble silicates and which are capable of inhibiting corrosion of metals in aqueous systems.

77 Claims, No Drawings

STABILIZATION OF AQUEOUS SILICATES USING ALKALI SILICONATES OF SILYLALKYL PHOSPHONATES

BACKGROUND OF THE INVENTION

This application is a continuation of application Ser. No. 891,584, filed Mar. 30, 1978, now abandoned.

This invention relates to novel silylalkylphosphonates and their use in the stabilization of aqueous silicates and as metal corrosion inhibitors.

Aqueous silicates as a class of compounds have been known for a long time as metal corrosion inhibitors for aqueous systems. One of the disadvantages of the silicates, however, is the fact that they are unstable and after use at elevated temperatures tend to gel and precipitate out of solution. There have been many efforts therefore to stabilize silicates so that they could be more persistent in their corrosion inhibiting properties.

Arthur N. Pines et al. in U.S. Pat. Nos. 3,312,622 and 3,198,820 describes combinations of silicone-silicate polymers as corrosion inhibitors. Although the patent does not specifically describe the stabilization of silicates, it is very obvious from the specification that the so-called "novel organosilicon polymer" does in fact contribute to the persistency of the corrosion inhibition of the silicone-silicate polymers of that invention. The novelty, as pointed out therein, is the use of silyl cationic carboxylates in conjunction with the silicates. Such materials are discussed as enhancing the corrosion inhibition of common antifreeze compositions and overcome disadvantages of other prior art corrosion inhibitors such as handling and dispensing of the antifreezes; selective corrosion inhibition of certain metals, poor shelf life, tendency to attack rubber hoses, excessive foaming in use and the causing of alcohols to decompose.

In later issued patents, U.S. Pat. Nos. 3,341,469 and 3,337,496, Pines et al. describes another system that was found useful for inhibiting corrosion in aqueous alcohol compositions. It consisted of a mixture of an alkyl silsesquioxane, a siloxane modified with a cyanoalkyl or carbinol group and, a silicate. These materials are stated as being "remarkably soluble in aqueous liquids". Further, the compositions are alleged to overcome many of the above mentioned disadvantages.

Finally, U.S. Pat. No. 3,948,964 issued Apr. 6, 1976 describes the stabilization of partially hydrolyzed silicic acid esters using stabilizers selected from organic compounds such as cyclic ethers, ether alcohols, carboxylic acid esters and ketones. Such stabilized materials are described as binders for zinc dust pigments and the like.

None of the above references, however, describe the compositions of the instant invention. The advantages of the prior art methods can be obtained with the instant invention and additional advantages over the prior art are obtained by this invention. Most notable are the advantages of low cost, enhanced effectiveness in stabilization of silicates and the persistency of corrosion inhibition.

THE INVENTION

This invention consists of several aspects of the same concept and one aspect is a composition of matter which is an alkali siliconate silylalkylphosphonate which has the general formula

(I)

wherein M is selected from a group consisting essentially of alkaline metal cations selected from a group consisting of sodium, potassium, lithium and rubidium and tetraorgano ammonium cations; R is a divalent aliphatic hydrocarbon radical containing 1-3 carbon atoms or the benzylene radical; P is the phosphorus atom and, R' is a hydrocarbon radical containing from 1-7 carbon atoms.

The phosphonate is derived from silylalkylesters of phosphorus by the reaction of an alkali metal hydroxide with the esters of phosphorus.

The precursor phosphorus compound, that is, the silylalkylesters of phosphorus can be prepared by several methods but it is preferred to prepare them by the method shown in the U.S. patent application Ser. No. 836,451, filed Sept. 26, 1977, now U.S. Pat. No. 4,093,641 in the name of Edwin P. Plueddemann. Plueddemann's method is easy to carry out and gives high yields which gives the resulting product a low cost. The precursor phosphorus compounds are then treated with dilute sodium hydroxide and refluxed for several hours to saponify the phosphonate precursor. The resulting product, in the case of the use of sodium hydroxide, is

i.e. the sodium salt of the sodium siliconate silylalkylphosphonate.

M in formula I can be independently an alkaline metal cation selected from sodium, potassium, lithium and rubidium and tetraorgano ammonium cations. Typical tetraorgano ammonium cations are tetramethyl ammonium and tetraethyl ammonium.

R in the above formula is a divalent aliphatic hydrocarbon radical containing 1-3 carbon atoms or the benzylene radical. The material should be water soluble so there is a limit to the size and type of R.

R' is a hydrocarbon radical of 1-7 carbon atoms and includes methyl, ethyl, phenyl, halobenzyl or the like.

In actual practice, using a dichlorobenzyldimethylphosphate as an example, the preparation is as follows:

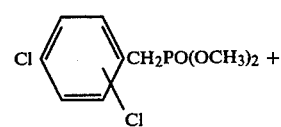

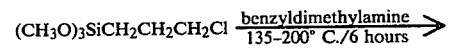

-continued

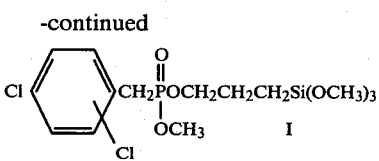

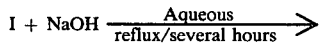

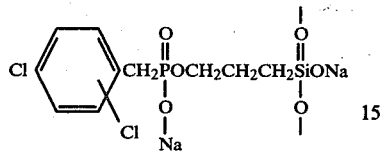

The resulting product is used alone or in conjunction with a silicate as will be explained infra.

As mentioned earlier, the products of the invention, the alkali siliconate silylalkylphosphonates are able to stabilize silicates that are useful as corrosion inhibitors for metals. Thus, obvious uses for such materials is in antifreeze compositions where metal corrosion is common due to high temperatures which cause decomposition of the alcohols typically used as freezing point depressants. If the silicates protect the internal metal parts of a cooling system, such as an automobile engine, and if the silicates can be induced to have persistency in the aqueous system, then there is a distinct advantage.

This invention therefore also contemplates a composition of matter which is an improved corrosion inhibiting alcohol composition consisting essentially of an alcohol and, as a corrosion inhibitor, a corrosion inhibiting amount of a composition consisting essentially of a combination of (A) an alkali siliconate silylalkylphosphonate which has the general formula

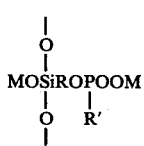 (II)

wherein M is independently an alkaline metal cation selected from the group consisting of sodium, potassium, lithium, rubidium and tetraorgano ammonium cations; R is a divalent aliphatic hydrocarbon radical containing 1-3 carbon atoms or the benzylene radical; P is the phosphorus atom and R' is a hydrocarbon radical containing from 1-7 carbon atoms, with (B) a soluble silicate represented by the general formula

wherein M has the meaning above and a has a value of 1-3.

It is contemplated that the alcohol composition can be anhydrous or contain, in addition to the alcohol and phosphonate-silicate, relatively small amounts of water and it is also contemplated that the alcohol composition can contain relatively large amounts of water, that is, the alcohol compositions may be "concentrates" or "coolants".

The alcohols that are useful in this invention include both monomeric alcohols such as methanol, ethanol, propanol and butanol and polyhydric alcohols such as ethylene glycol, diethylene glycol, triethylene glycol, propylene glycol, glycerol and mixtures of the above. What is contemplated are the currently useful antifreeze alcohols, especially ethylene glycol.

The corrosion inhibitor of the above composition is a composition of matter which consists essentially of (A) 0.1 to 99.9 parts by weight of an alkali siliconate silylalkylphosphonate which has the general formula

wherein M is independently an alkaline metal cation selected from the group consisting of sodium, potassium, lithium, rubidium and tetraorgano ammonium cations; R is a divalent aliphatic hydrocarbon radical containing 1-3 carbon atoms or the benzylene radical; P is the phosphorus atom and, R' is a hydrocarbon radical containing from 1-7 carbon atoms, with (B) 99.9 to 0.1 parts by weight of a soluble silicate represented by the general formula

wherein M has the meaning above and a has a value of 1-3.

As indicated above, essentially all ratios of phosphonate (A) to silicate (B) are effective to produce a metal corrosion inhibiting material. The ratio of (A) to (B) depends on the particular system in which it is used. Therefore the ratio of (A) to (B) that is the most useful in this invention is dependent on the amount of water in the system, the amount and type of alcohol present, the temperature of the aqueous medium and other additives or chemicals in the system.

The phosphonates have been discussed above and therefore, turning to component (B) of this invention, it should be noted that the silicates intended herein are the water soluble silicates and are represented by formula II as shown above. M in that formula has the same meaning as set forth above for M and is a cation which would render the silicate water soluble. Illustrative of these silicates are the alkali metal orthosilicates, alkali metal metasilicates, the alkali metal tetrasilicates, the alkali metal disilicates and the tetraorganoammonium silicates.

Specific examples of these silicates are potassium metasilicate, sodium orthosilicate, potassium disilicate, lithium orthosilicate, lithium metasilicate, lithium disilicate, rubidium disilicate, rubidium tetrasilicate, mixed silicates (e.g. $Na_2O.Li_2O.2SiO_2$ and $K_2O.Li_2O.4SiO_2$), tetra(methyl) ammonium silicate, tetra(ethyl) ammonium silicate, phenyltrimethyl ammonium silicate, benzyltrimethyl ammonium silicate, guanidine silicate and tetra(hydroxyethyl) ammonium silicate. The preferred silicates are sodium and potassium silicates, especially sodium disilicate and potassium disilicate.

The silicate used in producing the phosphonate-silicate inhibitor can be added to the reaction mixture as such or it can be formed in-situ by adding the appropriate alkali hydroxide and silicate to the reaction mixture.

It is contemplated within the scope of this invention that the combination (A) and (B) can be mixtures of (A) and (B) or partial reaction products of (A) and (B) or mixtures of mixtures of (A) and (B) and partial reaction products of (A) and (B).

The phosphonate-silicate combinations can be prepared by simply mixing the components (A) and (B), in the proper ratios, and stirring to homogenize them.

The phosphonaate-silicate combination is then added to the alcohol composition. The order in which the phosphonate, silicate and alcohol are added is not critical as long as the materials are thoroughly mixed.

The alcoholic phosphonate-silicate combinations are found to be useful in other areas besides automotive engine cooling. For example, the materials can be used in refrigeration and air conditioning units, cooling coils, heat exchangers and the like.

It was indicated earlier that the phosphonate could be useful in this invention without actually combining it with a silicate before use, that is, the phosphonate could be added to aqueous systems without the silicate. This invention therefore contemplates the use of the phosphonate and the phosphonate-silicate compositions in aqueous systems other than anti-freeze systems, that is, non-alcoholic aqueous systems which come in contact with metal surfaces i.e. such uses as controlling scale in geothermal power plants, scale control in conventional heat exchange systems and the like.

The amount of the combination (A) and (B) required to protect metals from corrosion depends on the metals to be protected, the system in which the combination is used, the temperature of the system and the other components and additives used in the system. Generally, the combination (A) and (B) is used in an amount as low as 20 parts per million up to 2 parts per 100 parts based on the weight of the aqueous liquid used.

For automotive engine coolants, it has been found that 200 parts of the phosphonate-silicate, based on a million parts of the aqueous alcohol coolant is effective to prevent corrosion. In non-alcoholic aqueous mediums, larger quantities are sometimes necessary. The preferred range of use for all systems within the scope of this invention is 200 parts per million parts of aqueous medium to 2 parts per 100 of aqueous medium.

It is within the scope of this invention to add various additives which impart special properties such as anti-foam agents, both organic and siloxane based, dyes, pH indicators, other inhibitors, thickeners and the like.

The following examples are shown to illustrate the invention and are not intended to define the scope thereof.

EXAMPLE 1

As indicated above, the materials of the art are subjected to very adverse conditions which affect their stabilizing properties. The materials of the instant invention were therefore subjected to adverse conditions in the following manner:

Myacol ® 215, a commercial silica sol manufactured by Nyanza, Inc., Ashland, MA 01721 was used in this example. The sol, which had a pH of 10.5 and which was Na+ stabilized, contained approximately 15% silica which had a particle size of approximately 2 m$\mu$m. The pH was reduced using 10% aqueous HCl solution as shown in Table I. The freeze-thaw cycle consisted of placing 1 oz. glass vials of the solutions in a freezer and freezing for twelve (12) hours. The vials were then removed from the freezer and allowed to thaw. The solutions were then checked for the appearance of precipitate indicating the solution was not stable.

EXAMPLE 2

To show the versatility of the materials, a second colloidal silica was treated and subjected to similar adverse conditions. See Table II. The silicate was Ludox ® as manufactured by E. I. DuPont De Nemours and Co., Wilmington, Del. The sol contains 30% silica and is ammonia stabilized. The pH of the sol was 9.4 and it had an average particle size of 13–14 m$\mu$. The pH was reduced by the addition of 10% aqueous HCl solution as shown in Table II.

EXAMPLE 3

This example illustrates the stabilizing effect of the material in Nalcoag ® 1034A manufactured by the Nalco Chemical Co., Chicago, IL 60601. The sol is H+ stabilized and contains 34% silica. It has an acid pH of 3.1 and the average particle size is 16–22 m$\mu$.

The Nalcoag was made less acid by the addition of ammonia before being tested as shown in Table III.

EXAMPLE 4

This example illustrates the stabilizing effect of the material in Ludox ® SM 30 manufactured by E. I. DuPont De Nemours and Co., Wilmington, Del. The sol is Na+ stabilized, has a pH of 9–10 and an average particle size of 7–8 m$\mu$. The solutions were tested as shown in Table IV after being reduced in pH by the addition of 10% aqueous HCl.

EXAMPLE 5

This example illustrates the effect of pH on stability. Stability of silicate/siliconate mixtures has a minimum generally at pH 8.

A 7.5:1 mol ratio of sodium silicate "G" to product was used. The silicate "G" was a sodium silicate manufactured by Philadelphia Quartz Co. and a weight ratio of SiO$_2$/Na$_2$O of 3.22 and a pH of 10.8. The product of this invention was a 1 molal aqueous siliconate i.e.

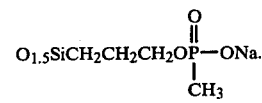

The mixture, after aging 1 day at room temperature, was acidified with 10% aqueous HCl to various pH's and observed for gel time.

| pH | gel time |
| --- | --- |
| 4 | >1 week |
| 6 | >1 week |
| 7 | >1 week |
| 8 | 1¾ hrs. |
| 9 | 9 hrs. |
| 10 | >1 week |

The sample at the pH of 4 showed no gelling at 1 year.

EXAMPLE 6

This example illustrates the effect of aging. A similar mixture as was prepared in Example 5 above was used for this example except the one (1) molal solution was 5:1 ratio of the silicate to the product.

| Sample | Time Aged At Room Temp. | Stability At pH 8 |
|---|---|---|
| A | 10 sec. | 30 sec. |
| B | 1 min. | 70 sec. |
| C | 5 min. | 20 min. |
| D | 15 min. | >1 week |
| E | 45 min. | >1 week |

Samples D and E were still stable at this writing, some four weeks (4) from their preparation.

EXAMPLE 7

This example shows the effect with sodium metasilicate, a low molecular weight silicate. A two molal sodium metasilicate solution was mixed with a two molal product i.e.

$$O_{1.5}SiCH_2CH_2CH_2OPONa$$
$$\underset{CH_3}{|}$$
(with P=O)

in a mol ratio of 7:3. After aging at room temperature for 6 months, the equilibrated mixture was further diluted with sodium metasilicate as indicated and then the pH was adjusted to 8 with a 10% aqueous HCl solution and the solutions were then observed for stability.

|  | mol ratio sodium metasilicate/phosphonate | | |
|---|---|---|---|
|  | 7:3 | 4:1 | 6:1 |
| Stability at pH 8 | >1 week | >1 week | 16 min. |

Therefore, it can be observed that a mixture of sodium metasilicate and a phosphonate of this invention, at a ratio of 4:1 provide stable corrosion inhibitors that will not gel when neutralized. A fresh mixture at a ratio of 4:1 gelled in 6 minutes at pH 8, indicating that a period of equilibration is beneficial.

EXAMPLE 8

Stabilization of a potassium silicate (Kasil 6).

A one (1) molal potassium silicate solution of weight ratio of $SiO_2/K_2O$ of 2.10 (mol ratio 3.3:1) manufactured by Philadelphia Quartz, was mixed with two ratios of 1 molal siliconate solutions and after aging 15 minutes the pH was adjusted to 8 with aqueous 10% HCl.

| Sample | Siliconate | Stability at pH 8 7.5:1 | Stability at pH 8 5:1 |
|---|---|---|---|
| A | $O_{1.5}SiCH_2CH_2COONa$ | 3 min. | >1 week |
| B | $O_{1.5}SiCH_2CH_2CH_2COONa$ | — | >1 week |
| C | $O_{1.5}SiCH_2CH_2CH_2P(ONa)_2$ (P=O) | 0.5 min | 1 min. |
| D | $O_{1.5}SiCH_2CH_2CH_2OP(ONa)_2$ (P=O) | 10 min. | >1 week |
| E | $O_{1.5}SiCH_2CH_2CH_2OPONa$ with $CH_3$ (P=O) | 10 min. | >1 week |

Samples A, B, D and E still show excellent stability after 4 weeks at ratio 5:1.

TABLE I

| Colloidal Silica (Silicate) | Parts Per Hundred Siliconate | Stability Under Adverse Conditions As a Measure of Time | |
|---|---|---|---|
| | | Room Temp. pH 5 | Freeze-thaw Cycling |
| Nyacol 215 | none | 0.4 hours | 70% precipitate |
| Nyacol 215 | 0.2 $O_{1.5}SiCCCOPONa$ with $CH_3$ (P=O) | 2 hours | 67% precipitate |
| Nyacol 215 | 2.0 $O_{1.5}SiCCCOPONa$ with $CH_3$ (P=O) | 32 hours | No precipitate stable |
| Nyacol 215 | 2.0 $O_{1.5}SiCCCOPONa$ with $OH$ (P=O) | 1.3 hours | No precipitate stable |

TABLE II

| Colloidal Silica (Silicate) | Parts Per Hundred Siliconate | Stability Under Adverse Conditions As a Measure of Time | | |
|---|---|---|---|---|
| | | Room Temp. pH 5 | 0.1N NaCl pH 6 | Freeze-thaw Cycling |
| Ludox AS | control | 2 hrs. | 0.5 hrs. | gel |
| Ludox AS | 0.2 $O_{1.5}SiCCCOPONa$ with $CH_3$ (P=O) | >50 hrs. | 50 hrs. | gel |
| Ludox AS | 2.0 $O_{1.5}SiCCCOPONa$ with $CH_3$ (P=O) | >100 hrs. | >144 hrs. | No precipitate |
| Ludox AS | 2.0 $O_{1.5}SiCCCOPONa$ with $OH$ (P=O) | >100 hrs. | >144 hrs. | No precipitate |

TABLE III

| Colloidal Silica (Silicate) | Parts Per Hundred Siliconate | Stability Under Adverse Conditions As a Measure of Time | | |
|---|---|---|---|---|
| | | pH 7 95° C. | pH 6 60° 0.1N HCl | Freeze-thaw Cycling |
| Nalcoag | control | 24 hrs. | 0.5 hr. | hazy |
| Nalcoag 1034A | 0.2 $O_{1.5}SiCCCOPONa$ with $\overset{O}{\|}$ above P, $CH_3$ below P | 36 hrs. | 0.7 hr. | gel |
| Nalcoag 1034A | 2.0 $O_{1.5}SiCCCOPONa$ with $\overset{O}{\|}$ above P, $CH_3$ below P | 72 hrs. | >120 hrs. | gel |
| Nalcoag 1034A | 2.0 $O_{1.5}SiCCCOPONa$ with $\overset{O}{\|}$ above P, $OH$ below P | 24 hrs. | >120 hrs. | clear |

TABLE IV

| Colloidal Silica (Silicate) | Parts Per Hundred Siliconate | Stability Under Adverse Conditions As a Measure of Time | |
|---|---|---|---|
| | | Room Temp. pH 5 | Freeze-thaw Cycling |
| Ludox SM | control | 2 hrs. | gel |
| Ludox SM | 0.2 $O_{1.5}SiCCCOPONa$ with $\overset{O}{\|}$ above P, $CH_3$ below P | 50 hrs. | gel |
| Ludox SM | 2.0 $O_{1.5}SiCCCOPONa$ with $\overset{O}{\|}$ above P, $CH_3$ below P | 20 hrs. | clear |
| Ludox SM | 2.0 $O_{1.5}SiCCCOPONa$ with $\overset{O}{\|}$ above P, $OH$ below P | 120 hrs. | clear |

That which is claimed is:

1. A composition of matter which is an alkali siliconate silylalkyl phosphonate which has the general formula

wherein

M is selected from a group consisting essentially of alkaline metal cations selected from a group consisting of sodium, potassium, lithium and rubidium and tetraorgano ammonium cations;

R is a divalent aliphatic hydrocarbon radical containing 1–3 carbon atoms or the benzylene radical;

P is the phosphorus atom and,

R' is a hydrocarbon radical containing from 1–7 carbon atoms.

2. A composition of matter as claimed in claim 1 wherein M in each case is sodium, R is $+CH_2+_x$ wherein x is 3 and R' is methyl.

3. A composition of matter as claimed in claim 1 wherein M in each case is potassium, R is $+CH_2+_x$ wherein x is 3 and R' is methyl.

4. A composition of matter as claimed in claim 1 wherein M in each case is lithium, R is $+CH_2+_x$ wherein x is 3 and R' is methyl.

5. A composition of matter as claimed in claim 1 wherein M in each case is tetraorganoammonium cations, R is $+CH_2+_x$ wherein x is 3 and R' is methyl.

6. A composition of matter as claimed in claim 1 wherein M in each case is sodium, R is $+CH_2+_x$ wherein x is 2 and R' is methyl.

7. A composition of matter as claimed in claim 1 wherein M in each case is potassium, R is $+CH_2+_x$ wherein x is 2 and R' is methyl.

8. A composition of matter as claimed in claim 1 wherein M in each case is lithium, R is $+CH_2+_x$ wherein x is 2 and R' is methyl.

9. A composition of matter as claimed in claim 1 wherein M in each case is tetraorganoammonium cations, R is $+CH_2+_x$ wherein x is 2 and R' is methyl.

10. A composition of matter as claimed in claim 1 wherein M in each case is sodium, R is $+CH_2+_x$ wherein x is 3 and R' is ethyl.

11. A composition of matter as claimed in claim 1 wherein M in each case is potassium, R is $+CH_2+_x$ wherein x is 3 and R' is ethyl.

12. A composition of matter as claimed in claim 1 wherein M in each case is lithium, R is $+CH_2+_x$ wherein x is 3 and R' is ethyl.

13. A composition of matter as claimed in claim 1 wherein M in each case is a tetraorganoammonium cation, R is $+CH_2+_x$ wherein x is 3 and R' is ethyl.

14. A composition of matter as claimed in claim 1 wherein M in each case is sodium, R is $+CH_2+_x$ wherein x is 2 and R' is ethyl.

15. A composition of matter as claimed in claim 1 wherein M in each case is potassium, R is $+CH_2+_x$ wherein x is 2 and R' is ethyl.

16. A composition of matter as claimed in claim 1 wherein M in each case is lithium, R is $+CH_2+_x$ wherein x is 2 and R' is ethyl.

17. A composition of matter as claimed in claim 1 wherein M in each case is a tetraorganoammonium cation, R is $+CH_2+_x$ wherein x is 2 and R' is ethyl.

18. An improved corrosion inhibiting alcohol composition consisting essentially of an alcohol selected from the group consisting essentially of (A) monomeric alcohols, (B) polyhydric alcohols and (C) mixtures of (A) and (B) and, as a corrosion inhibitor, 20 to 20,000 parts per million based on the weight of the corrosion inhibiting alcohol composition of a composition consisting essentially of a combination of (A) 0.1 to 99.9 parts by weight of an alkali siliconate silylalkylphosphonate which has the general formula

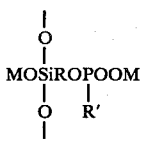

wherein
- M is independently an alkaline metal cation selected from the group consisting of sodium, potassium, lithium, rubidium and tetraorgano ammonium, cations;
- R is a divalent aliphatic hydrocarbon radical containing 1-3 carbon atoms or the benzylene radical;
- P is the phosphorus atom and
- R' is a hydrocarbon radical containing from 1-7 carbon atoms, with (B) 99.9 to 0.1 parts by weight of a soluble silicate represented by the general formula

wherein M has the meaning above and a has a value of 1-3.

19. An alcohol composition as claimed in claim 18 wherein the alcohol is propylene glycol.

20. An alcohol composition as claimed in claim 18 wherein the alcohol is ethylene glycol.

21. An alcohol composition as claimed in claim 19 wherein in component (A), M in each case is sodium, R is $+CH_2+_x$ wherein x is 3 and R' is methyl.

22. A alcohol composition as claimed in claim 19 wherein in component (A), M in each case is potassium, R is $+CH_2+_x$ wherein x is 3 and R' is methyl.

23. An alcohol composition as claimed in claim 19 wherein in component (A), M in each case is lithium, R is $+CH_2+_x$ wherein x is 3 and R' is methyl.

24. An alcohol composition as claimed in claim 19 wherein in component (A), M in each case is tetraorganoammonium cations, R is $+CH_2+_x$ wherein x is 3 and R' is methyl.

25. An alcohol composition as claimed in claim 19 wherein in component (A), M in each case is sodium, R is $+CH_2+_x$ wherein x is 2 and R' is methyl.

26. An alcohol composition as claimed in claim 19 wherein in component (A), M in each case is potassium, R is $+CH_2+_x$ wherein x is 2 and R' is methyl.

27. An alcohol composition as claimed in claim 19 wherein in component (A), M in each case is lithium, R is $+CH_2+_x$ wherein x is 2 and R' is methyl.

28. An alcohol composition as claimed in claim 19 wherein in component (A), M in each case is tetraorganoammonium cations, R is $+CH_2+_x$ wherein x is 2 and R' is methyl.

29. An alcohol composition as claimed in claim 19 wherein in component (A), M in each case is sodium, R is $+CH_2+_x$ wherein x is 3 and R' is ethyl.

30. An alcohol composition as claimed in claim 19 wherein in component (A), M in each case is potassium, R is $+CH_2+_x$ wherein x is 3 and R' is ethyl.

31. An alcohol composition as claimed in claim 19 wherein in component (A), M in each case is lithium, R is $+CH_2+_x$ wherein x is 3 and R' is ethyl.

32. An alcohol composition as claimed in claim 19 wherein in component (A), M in each case is a tetraorganoammonium cation, R is $+CH_2+_x$ wherein x is 3 and R' is ethyl.

33. An alcohol composition as claimed in claim 19 wherein the glycol is admixed with water.

34. An alcohol composition as claimed in claim 21 wherein M in component (B) is sodium.

35. An alcohol composition as claimed in claim 22 wherein M in component (B) is potassium.

36. An alcohol composition as claimed in claim 23 wherein M in component (B) is lithium.

37. An alcohol composition as claimed in claim 24 wherein M in component (B) is a tetraorganoammonium cation.

38. A composition of matter which consists essentially of
(A) 0.1 to 99.9 parts by weight of an alkali siliconate silylalkylphosphonate which has the general formula

wherein
- M is independently an alkaline metal cation selected from the group consisting of sodium, potassium, lithium, rubidium and tetraorgano ammonium cations;
- R is a divalent aliphatic hydrocarbon radical containing 1-3 carbon atoms or the benzylene radical;
- P is the phosphorus atom and,
- R' is a hydrocarbon radical containing from 1-7 carbon atoms, with (B) 99.9 to 0.1 parts by weight of a soluble silicate represented by the general formula

wherein M has the meaning above and a has a value of 1-3.

39. A composition as claimed in claim 38 wherein in component (A), M in each case is sodium, R is $+CH_2+_x$ wherein x is 3 and R' is methyl.

40. A composition as claimed in claim 38 wherein in component (A), M in each case is potassium, R is $+CH_2+_x$ wherein x is 3 and R' is methyl.

41. A composition as claimed in claim 38 wherein in component (A), M in each case is lithium, R is $+CH_2+_x$ wherein x is 3 and R' is methyl.

42. A composition as claimed in claim 38 wherein in component (A), M in each case is tetraorganoammonium cations, R is $+CH_2+_x$ wherein x is 3 and R' is methyl.

43. A composition as claimed in claim 38 wherein in component (A), M in each case is sodium, R is $+CH_2+_x$ wherein x is 2 and R' is methyl.

44. A composition as claimed in claim 38 wherein in component (A), M in each case is potassium, R is $+CH_2+_x$ wherein x is 2 and R' is methyl.

45. A composition as claimed in claim 38 wherein in component (A), M in each case is lithium, R is $+CH_2+_x$ wherein x is 2 and R' is methyl.

46. A composition as claimed in claim 38 wherein in component (A), M in each case is tetraorganoammonium cations, R is $+CH_2+_x$ wherein x is 2 and R' is methyl.

47. A composition as claimed in claim 38 wherein in component (A), M in each case is sodium, R is $+CH_2+_x$ wherein x is 3 and R' is ethyl.

48. A composition as claimed in claim 38 wherein in component (A), M in each case is potassium, R is $+CH_2+_x$ wherein x is 3 and R' is ethyl.

49. A composition as claimed in claim 38 wherein in component (A), M in each case is lithium, R is $+CH_2+_x$ wherein x is 3 and R' is ethyl.

50. A composition as claimed in claim 38 wherein in component (A), M in each case is a tetraorganoammonium cation, R is $+CH_2+_x$ wherein x is 3 and R' is ethyl.

51. A method of stabilizing soluble silicates comprising adding to 99.9 to 0.1 parts by weight of the soluble silicates, 0.1 to 99.9 parts by weight of a composition consisting essentially of an alkali siliconate silylalkylphosphonate which has the general formula

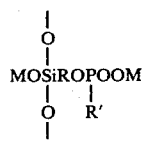

wherein
M is selected from the group consisting essentially of alkaline metal cations selected from a group consisting of sodium, potassium, lithium and rubidium and tetraorgano ammonium cations;
R is a divalent aliphatic hydrocarbon radical containing 1-3 carbon atoms or the benzylene radical;
P is the phosphorus atom and,
R' is a hydrocarbon radical containing from 1-7 carbon atoms.

52. A method as claimed in claim 51 wherein M in the formula, in each case, is sodium, R is $+CH_2+_x$ wherein x is 3 and R' is methyl.

53. A method as claimed in claim 51 wherein M in the formula, in each case, is potassium, R is $+CH_2+_x$ wherein x is 3 and R' is methyl.

54. A method as claimed in claim 51 wherein M in the formula, in each case, is lithium, R is $+CH_2+_x$ wherein x is 3 and R' is methyl.

55. A method as claimed in claim 51 wherein M in the formula, in each case, is a tetraorganoammonium cation, R is $+CH_2+_x$ wherein x is 3 and R' is methyl.

56. A method as claimed in claim 51 wherein M in the formula, in each case is sodium, R is $+CH_2+_x$ wherein x is 2 and R' is methyl.

57. A method as claimed in claim 51 wherein M in the formula, in each case, is potassium, R is $+CH_2+_x$ wherein x is 2 and R' is methyl.

58. A method as claimed in claim 51 wherein M in the formula, in each case, is lithium, R is $+CH_2+_x$ wherein x is 2 and R' is methyl.

59. A method as claimed in claim 51 wherein M in the formula, in each case, is a tetraorganoammonium cation, R is $+CH_2+_x$ wherein x is 2 and R' is methyl.

60. A method of inhibiting metal corrosion in an aqueous medium by adding to the aqueous medium a composition consisting essentially of an alkali siliconate silylalkylphosphonate which has the general formula

wherein
M is selected from a group consisting essentially of alkaline metal cations selected from a group consisting of sodium, potassium, lithium and rubidium and tetraorgano ammonium cations;
R is a divalent aliphatic hydrocarbon radical containing 1-3 carbon atoms or the benzylene radical;
P is the phosphorus atom and,
R' is a hydrocarbon radical containing from 1-7 carbon atoms.

61. A method as claimed in claim 60 wherein M in the formula, in each case, is sodium, R is $+CH_2+_x$ wherein x is 3 and R' is methyl.

62. A method as claimed in claim 60 wherein M in the formula, in each case, is potassium, R is $+CH_2+_x$ wherein x is 3 and R' is methyl.

63. A method as claimed in claim 60 wherein M in the formula, in each case, is lithium, R is $+CH_2+_x$ wherein x is 3 and R' is methyl.

64. A method as claimed in claim 60 wherein M in the formula, in each case, is a tetraorganoammonium cation, R is $+CH_2+_x$ wherein x is 3 and R' is methyl.

65. A method as claimed in claim 60 wherein M in the formula, in each case, is sodium, R is $+CH_2+_x$ wherein x is 2 and R' is methyl.

66. A method as claimed in claim 60 wherein M in the formula, in each case, is potassium, R is $+CH_2+_x$ wherein x is 2 and R' is methyl.

67. A method as claimed in claim 60 wherein M in the formula, in each case, is lithium, R is $+CH_2+_x$ wherein x is 2 and R' is methyl.

68. A method as claimed in claim 60 wherein M in the formula, in each case, is a tetraorganoammonium cation, R is $+CH_2+_x$ wherein x is 2 and R' is methyl.

69. A method of inhibiting metal corrosion in an aqueous medium by adding to the aqueous medium a composition consisting essentially of
(A) 0.1 to 99.9 parts by weight of an alkali siliconate silylalkylphosphonate which has the general formula

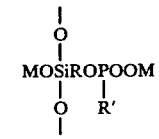

wherein
M is independently an alkaline metal cation selected from the group consisting of sodium, potassium, lithium, rubidium and tetraorgano ammonium cations;
R is a divalent aliphatic hydrocarbon radical containing 1-3 carbon atoms or the benzylene radical;

P is the phosphorus atom and,

R' is a hydrocarbon radical containing from 1–7 carbon atoms, with (B) 99.9 to 0.1 parts by weight of a soluble silicate represented by the general formula $$(MO)_a SiO_{(4-a)/2}$$

wherein M has the meaning above and a has a value of 1–3.

70. A method as claimed in claim 69 wherein in component (A), M in each case is sodium, R is $-(CH_2)_x$ is 3 and R' is methyl.

71. A method as claimed in claim 69 wherein in component (A), M in each case is potassium, R is $-(CH_2)_x$ wherein x is 3 and R' is methyl.

72. A method as claimed in claim 69 wherein in component (A), M in each case is lithium, R is $-(CH_2)_x$ wherein x is 3 and R' is methyl.

73. A method as claimed in claim 69 wherein in component (A), M in each case is tetraorganoammonium cations, R is $-(CH_2)_x$ wherein x is 3 and R' is methyl.

74. A method as claimed in claim 69 wherein in component (A), M in each case is sodium, R is $-(CH_2)_x$ wherein x is 2 and R' is methyl.

75. A method as claimed in claim 69 wherein in component (A), M in each case is potassium, R is $-(CH_2)_x$ wherein x is 2 and R' is methyl.

76. A method as claimed in claim 69 wherein in component (A), M in each case is lithium, R is $-(CH_2)_x$ wherein x is 2 and R' is methyl.

77. A method as claimed in claim 69 wherein in component (A), M in each case is tetraorganoammonium cations, R is $-(CH_2)_x$ wherein x is 2 and R' is methyl.

* * * * *

UNITED STATES PATENT AND TRADEMARK OFFICE
CERTIFICATE OF CORRECTION

PATENT NO. : 4,370,255

DATED : January 25, 1983

INVENTOR(S) : Edwin P. Plueddemann

It is certified that error appears in the above-identified patent and that said Letters Patent is hereby corrected as shown below:

In column 3, line 58; column 4, line 31; column 9, line 7; column 11, line 26; column 12, line 44; and column 15, line 10, "and a has" should read -- and $\underline{a}$ has --.

In column 4, line 58, "$Na_2O.Li_2O.2SiO_2$ and $K_2O.Li_2O.4SiO_2$)," should read -- $Na_2O \cdot Li_2O \cdot 2SiO_2$ and $K_2O \cdot Li_2O \cdot 4SiO_2$), --.

In column 6, line 39, "and a weight" should read -- and has a weight --.

In column 8, line 16, "Colloidal" should be directly above "Silica" in line 17.

In column 9, line 7, "Nalcoag" should read -- Nalcoag 1034A --.

Signed and Sealed this

Second Day of April 1985

[SEAL]

Attest:

DONALD J. QUIGG

Attesting Officer

Acting Commissioner of Patents and Trademarks